US009775647B2

(12) United States Patent
Schiffl et al.

(10) Patent No.: US 9,775,647 B2
(45) Date of Patent: Oct. 3, 2017

(54) MAGNESIUM ALLOY

(75) Inventors: Andreas Schiffl, Braunau am Inn (AT); Bernhard Mingler, Vienna (AT)

(73) Assignee: AIT AUSTRIAN INSTITUTE OF TECHNOLOGY GMBH, Vienna (AT)

( * ) Notice: Subject to any disclaimer, the term of this patent is extended or adjusted under 35 U.S.C. 154(b) by 95 days.

(21) Appl. No.: 13/700,858

(22) PCT Filed: Jun. 15, 2011

(86) PCT No.: PCT/AT2011/050001
§ 371 (c)(1),
(2), (4) Date: Feb. 11, 2013

(87) PCT Pub. No.: WO2012/003522
PCT Pub. Date: Jan. 12, 2012

(65) Prior Publication Data
US 2013/0144290 A1  Jun. 6, 2013

(30) Foreign Application Priority Data
Jul. 6, 2010 (AT) .............................. A 1134/2010

(51) Int. Cl.
A61B 17/72 (2006.01)
A61B 17/68 (2006.01)
(Continued)

(52) U.S. Cl.
CPC ............... *A61B 17/68* (2013.01); *A61F 2/00* (2013.01); *A61L 31/022* (2013.01);
(Continued)

(58) Field of Classification Search
USPC ....... 606/62–68; 148/666–667; 420/402–414
See application file for complete search history.

(56) References Cited

U.S. PATENT DOCUMENTS 6,767,506 B2 * 7/2004 Bronfin et al. ................ 420/411
2002/0020475 A1 * 2/2002 Sakamoto et al. ............ 148/667
(Continued)

FOREIGN PATENT DOCUMENTS

| EP | 1 842 507 | 10/2007 |
| WO | 2009/148515 | 12/2009 |
| WO | 2011/146970 | 12/2011 |

OTHER PUBLICATIONS

European Office action conducted in counterpart European Appln. No. 11 802 999.0 (Mar. 14, 2014).
(Continued)

*Primary Examiner* — Jan Christopher Merene
*Assistant Examiner* — Steven Cotroneo
(74) *Attorney, Agent, or Firm* — Greenblum & Bernstein, P.L.C.

(57) ABSTRACT

The invention relates to a magnesium alloy containing (in % by weight) more than 0.0 to 7.0% zinc, optionally more than 0.0 to 1.0% zirconium, optionally more than 0.0 to 1.0% calcium, optionally more than 0.0 to 1.0% manganese, optionally more than 0.0 to 0.5% silicon, optionally more than 0.0 to 1.0% silver, a max. up to 0.5% aluminum and at least one element selected from the group comprising more than 0.05 to 0.6% yttrium, more than 0.05 to 4.0% ytterbium, more than 0.05 to 4.0% gadolinium, with the residue being magnesium and impurities due to production. The invention also relates to a use of a magnesium alloy of this type and an implant therefrom and a method for producing a body of a magnesium alloy according to the invention.

20 Claims, 3 Drawing Sheets

Figure 1:
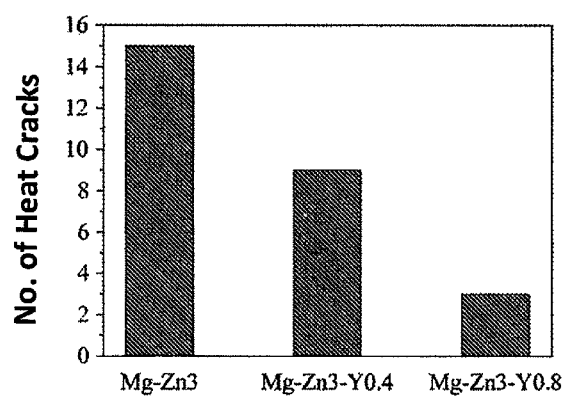

(51) Int. Cl.
    *C22C 23/04*     (2006.01)
    *C22F 1/06*     (2006.01)
    *A61F 2/00*     (2006.01)
    *C22C 23/02*     (2006.01)
    *C22C 23/06*     (2006.01)
    *A61L 31/02*     (2006.01)
    *A61L 31/14*     (2006.01)

(52) U.S. Cl.
    CPC ............ *A61L 31/148* (2013.01); *C22C 23/02* (2013.01); *C22C 23/04* (2013.01); *C22C 23/06* (2013.01); *C22F 1/06* (2013.01)

(56) References Cited

U.S. PATENT DOCUMENTS

| | | | | |
|---|---|---|---|---|
| 2003/0129074 A1* | 7/2003 | Bronfin et al. | ............... | 420/406 |
| 2004/0045639 A1* | 3/2004 | Kikawa | ................... | C22C 23/06 148/420 |
| 2005/0095166 A1* | 5/2005 | Saikawa | ................. | C22C 23/02 420/407 |
| 2006/0020289 A1* | 1/2006 | Kuttler | .................... | A61L 17/06 606/228 |
| 2008/0193322 A1* | 8/2008 | Gibson et al. | ................. | 420/405 |
| 2008/0262589 A1* | 10/2008 | Nagura | ................. | A61L 27/047 623/1.2 |
| 2012/0095463 A1* | 4/2012 | Rains et al. | ..................... | 606/63 |
| 2013/0199677 A1* | 8/2013 | Venkatesan | .......... | B22D 21/007 148/557 |
| 2014/0154341 A1* | 6/2014 | Manuel et al. | ............... | 424/682 |

OTHER PUBLICATIONS

Yu et al., "Microstructure and mechanical properties of ZK60-Yb magnesium alloys", Materials Science and Engineering A: Structural Materials: Properties, Microstructure & Processing, Lausanne, CH, Jan. 28, 2008, pp. 101-107, vol. 478, No. 1-2.

* cited by examiner

MAGNESIUM ALLOY

The invention relates to a magnesium alloy and the use thereof and an implant of a magnesium alloy.

Furthermore, the invention relates to a method for producing a body, in particular an implant, from a magnesium alloy.

In implant technology implants of magnesium alloys are currently being tested intensively as biodegradable medical products that are used in the human or animal body. The background thereby is that implants of magnesium alloys, depending on the nature of the respective alloy, can be dissolved by body fluids. It follows from this that bone nails or medullary nails or other implants of a biodegradable magnesium alloy can be used in a human or animal body and then, preferably after fulfilling a medical function, dissolve easily. This is a decisive advantage compared to conventional implants, since no further operation is necessary in order to remove an implant from the body after fulfilling a medical or therapeutic function. Ideally, the implant should remain stable as long as a medical or therapeutic function is desired and immediately thereafter should dissolve completely with the action of a body fluid.

In this context in particular magnesium zinc alloys are considered, since magnesium zinc alloys have high strength values which is necessary or at least can be necessary for the fulfillment of a medical or therapeutic function.

In order to achieve a required minimum strength for certain applications, magnesium zinc alloys are also frequently used in other fields. With alloys of this type, in particular with higher zinc contents, although bodies with high strength are produced, the inventors have recognized that there is often a high heat crack tendency during the production of the bodies (so-called "hot tearing"). However, a heat crack tendency can mean that a cast billet in the surface region, depending on a required quality, has to be processed by chip removal in order to obtain a material without defects for a further processing, in particular a production of end products. This requires a further process step, which not only entails additional expenditure in terms of time and work, but also leads to a considerable material waste. However, a heat crack tendency can also go so far that heat cracks are present in the center of a cast piece, which leads to the waste of the same. For example, a billet can no longer be pressed if there is a crack in the center of the billet.

The object of the invention is to disclose an alloy of the type mentioned at the outset in which a heat crack tendency is reduced.

A further object of the invention is to show a use of an alloy of this type.

Furthermore, it is an object of the invention to disclose an implant that can be produced in a cost-effective manner.

Finally, it is an object of the invention to disclose a method of the type mentioned at the outset with which a body can be produced from a magnesium alloy without heat cracks or at least with a reduced number of heat cracks.

The above-mentioned object is attained according to the invention by a magnesium alloy containing (in % by weight)
More than 0.0 to 7.0% zinc
Optionally more than 0.0 to 1.0% zirconium
Optionally more than 0.0 to 1.0% calcium
Optionally more than 0.0 to 1.0% manganese
Optionally more than 0.0 to 0.5% silicon
Optionally more than 0.0 to 1.0% silver
Max. up to 0.5% aluminum
And at least one element selected from the group comprising
More than 0.05 to 0.6% yttrium
More than 0.05 to 4.0% ytterbium
More than 0.05 to 4.0% gadolinium
The residue being magnesium and impurities due to production.

Within the scope of the invention it was recognized that in a magnesium zinc alloy even low yttrium and/or ytterbium and/or gadolinium contents lead to a clear reduction of a heat crack tendency of the magnesium alloy. This can be due to the fact that through the addition of corresponding elements during a production of a melt intermetallic phases are formed, whereby a solidus line is raised and a solidification range is decreased and thus a thermal shrinkage responsible for a heat crack tendency is reduced. At the same time a larger thermal window results thereby during a subsequent thermal treatment, in particular an extrusion, an extrusion molding or a rolling, since without partial melting the magnesium alloy can be thermally treated at much higher temperatures than previously known alloys of this type.

A magnesium alloy according to the invention contains zinc so that high mechanical characteristic values are obtained, which can be necessary for diverse applications such as stents. It is preferably provided that the magnesium alloy contains 1.0 to 5.0%, preferably 2.5 to 4.5% zinc. An alloy according to the invention can contain relatively high contents of zinc of e.g. more than 2.5%, which gives a desired high strength without there being a practically significant heat crack tendency.

Furthermore, a magnesium alloy according to the invention can contain zirconium and/or calcium up to respectively 1.0%, namely for the purpose of a grain refinement. It is preferably provided that the magnesium alloy contains more than 0.1 to 0.6% zirconium and/or more than 0.1 to 0.4% calcium.

Zirconium and calcium can also in principle be constituents of intermetallic phases, which are formed during the production of the magnesium alloy or cooling of a melt corresponding in the composition. In order not to prevent the formation of desired ternary intermetallic phases with the elements yttrium, ytterbium and/or gadolinium on the one hand, but on the other hand also to ensure a desired grain refinement, a sum content of zirconium and calcium is advantageously 0.6 to 1.0%.

Furthermore, a magnesium alloy according to the invention can comprise manganese, silicon and/or silver with the above-mentioned maximum contents. In particular it can be provided that the magnesium alloy contains at least one element selected from the group comprising
More than 0.1 to 0.5% manganese
More than 0.1 to 0.5% silicon
More than 0.1 to 0.5% silver.

Silver and silicon contribute to a fine granularity of a structure of the magnesium alloy. Manganese improves a corrosion resistance of the magnesium alloy.

Contents of the elements yttrium, ytterbium and/or gadolinium are preferably coordinated such that the magnesium alloy contains at least one element selected from the group comprising
More than 0.05 to less than 0.5% yttrium
More than 0.1 to 1.2% ytterbium
More than 0.1 to 1.2% gadolinium.

This is because compared to yttrium, ytterbium and gadolinium have approximately twice the atomic mass. So if the cited elements are present individually, twice the quantity of ytterbium or gadolinium is to be provided relative to yttrium in order to obtain intermetallic phases with analogous action. The cited lower limits of 0.05% for yttrium and 0.1% for ytterbium and gadolinium are thereby minimum contents that are necessary with respect to a formation of intermetallic phases. It is preferred that a lower limit is established at 0.1% for yttrium and respectively 0.2% for ytterbium and gadolinium. Maximum contents of 0.5% for yttrium and respectively 1.2% for ytterbium and gadolinium can be expedient in order on the one hand to impede a heat crack tendency but on the other hand to also keep a cytotoxicity of implants as low as possible. In particular it can also be provided that several of the cited elements are present at the same time, wherein a maximum sum content is less than 2.5%.

An aluminum content is limited to a maximum of up to 0.5% because aluminum can mask the advantageous effects of yttrium, ytterbium and/or gadolinium.

A magnesium alloy according to the invention can be used in all fields in which a low heat crack tendency is desirable, for example with a production of components for motor vehicles from high-strength magnesium alloys with a zinc content of more than 2.5%. However, it is preferably provided that a magnesium alloy according to the invention is used for the production of a biodegradable implant, in particular for use in a medullary cavity of a human body.

The further object of the invention is achieved if a method of the type mentioned at the outset comprises the following steps;
a) Production of a melt containing
More than 0.0 to 7.0% zinc
Optionally more than 0.0 to 1.0% zirconium
Optionally more than 0.0 to 1.0% calcium
Optionally more than 0.0 to 1.0% manganese
Optionally more than 0.0 to 0.5% silicon
Optionally more than 0.0 to 1.0% silver
A maximum of up to 0.5% aluminum
And at least one element selected from the group comprising
More than 0.05 to 0.6% yttrium
More than 0.05 to 4.0% ytterbium
More than 0.05 to 4.0% gadolinium
The residue being magnesium and impurities due to production,
b) Casting the melt to form a solid mass
c) Annealing the solid mass
d) Optionally shaping the solid mass or a part thereof,
e) Production of the body from the optionally shaped mass or parts thereof.

One advantage achieved with the invention is to be seen in that a body can be produced that has a low heat crack tendency. Complex processing operations leading to unnecessary waste, such as a chip removing processing of a surface of the body after the production of the same can thereby be omitted. Furthermore, a produced body in particular is suitable for further processing to form medical products, in particular implants for osteosynthesis, for example bone plates, bone screws, medullary screws or so-called Kirschner wires, It is an advantage thereby that the magnesium alloy dissolves by itself in the body after a predetermined time due to the action of body fluids. The provided element or elements yttrium, ytterbium and/or gadolinium ensure during production that a temperature window for a melt solidification is relatively small or a solidus line is raised compared to a magnesium zinc alloy, which leads to the desired reduction of a heat crack tendency even with zinc contents above 2.5%. The contents of the individual elements yttrium, ytterbium and/or gadolinium are thereby advantageously coordinated such that intermetallic phases form during a phase of the solidification of the melt due to the distribution coefficient, wherein under the influence of the segregation an increase in concentration of the element or elements takes place, the activity of which already leads at an early stage in a solidification range to the deposit of a ternary intermetallic compound or compounds of the element or elements with magnesium and zinc using the entire residual melt, whereby zinc is no longer available or is available only to a limited extent for a reaction otherwise occurring at much lower temperatures with the formation of a binary metallic compound of magnesium and zinc, which leads to a rise in the solidus line. Furthermore, contents of the elements yttrium, ytterbium and/or gadolinium are coordinated such that with the use of the magnesium alloy as an implant the intermetallic phases and the matrix dissolve at approximately the same speed, so that after the dissolution of the implant no undesirable cytotoxic constituents are present in the body.

A continuous casting is generally used as a casting method, although low-pressure die casting, die casting, sand casting and permanent mold casting methods can also be used. An annealing is preferably carried out at an annealing temperature of 280° C. to 400° C. If a shaping, e.g. an extrusion molding, equal channel angular pressing (also known as "ECAP") and/or forging is provided, this is carried out below the annealing temperature.

With a method according to the invention it can be an advantage to limit the contents of individual elements as listed above, in order to achieve the advantages likewise already described.

Figure 2:
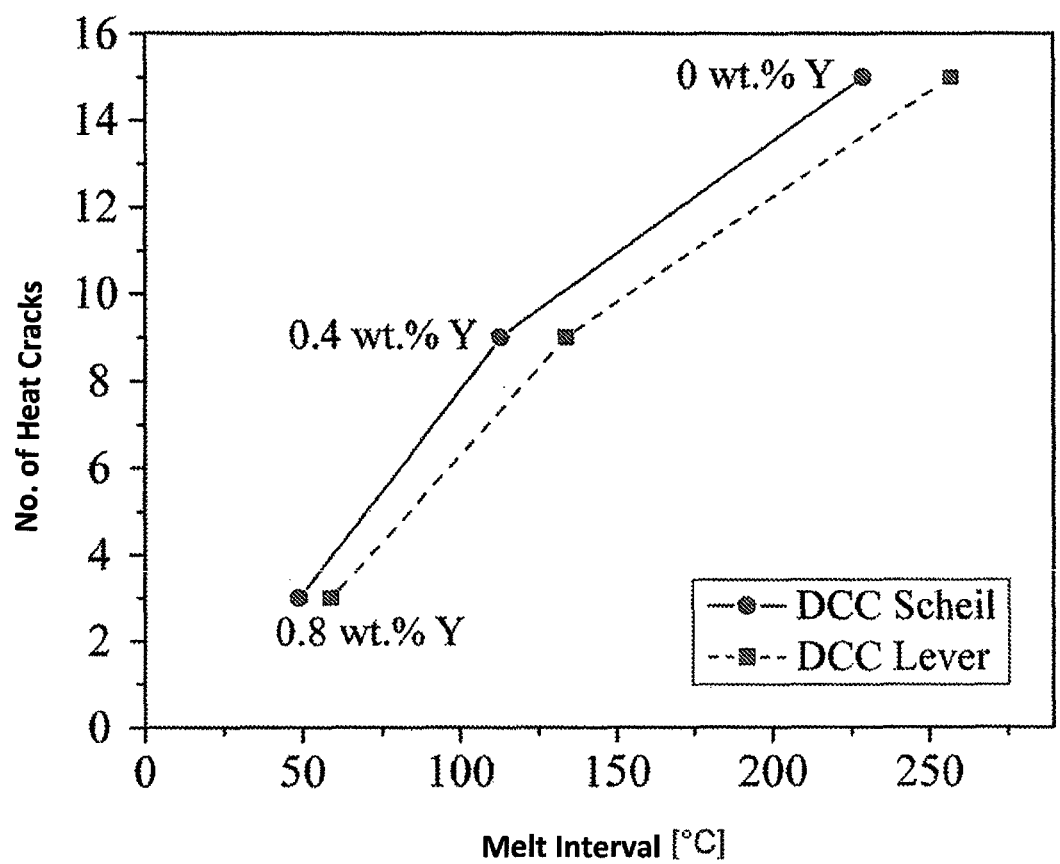
Figure 3:
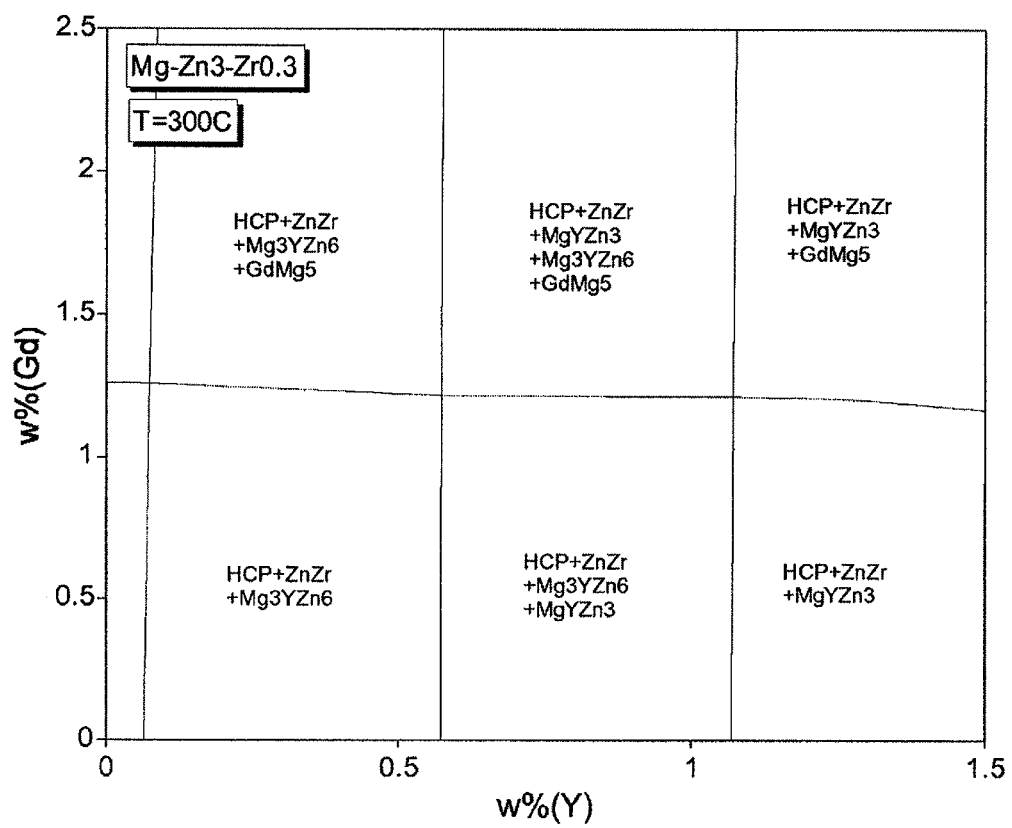

Further features, advantages and effects of the invention are shown by the exemplary embodiments represented below. The drawings, to which reference is made thereby, show:

FIG. 1 a diagram regarding a heat crack tendency;
FIG. 2 a diagram regarding a heat crack tendency as a function of a solidification range;
FIG. 3 an isothermal section at 300° C. for magnesium zinc alloys with different contents of yttrium and gadolinium.

Magnesium zinc alloys with different contents of yttrium, ytterbium and/or gadolinium were poured off at 700° C. into a star mold of a steel. The star-shaped components had elongated rod-shaped regions with a length of 25, 45, 65, 95, 125 and 175 mm; a diameter was constantly 10 mm. For each magnesium zinc alloy five such components were produced. The star mold of steel was heated to a temperature of 250±5° C. before pouring off. The casting temperature of 700° C. corresponded to an overheating of the melts of approx. 60° C. After the pouring off, the star mold was allowed to rest for five minutes and subsequently opened in order to test the poured molded parts.

In the above manner magnesium zinc alloys with yttrium contents of up to 0.8% were produced. In addition to magnesium, the alloys contained 3.0% zinc, approx. 0.4% zirconium, approx. 0.3% calcium and optionally 0.15% manganese, 0.4% to 0.8% yttrium and/or 2.0% ytterbium and/or 2.0% gadolinium.

The individual components were subsequently tested with respect to cracks, wherein an evaluation of the quality of the individual segments based on an optical examination of the elongated regions of the components was carried out. The samples were furthermore tested for cracks in the interior.

It was not possible to establish any cracks in the interior of the individual components. With respect to a number of cracks on a surface, for magnesium alloys produced with yttrium it was shown that no heat cracks or only a small number of heat cracks were present. The heat cracks decreased with increasing yttrium content. A similar picture resulted with further tests, wherein corresponding melts were produced not in star-shaped molds, but by so-called "direct chill casting" or by continuous casting; the corresponding data are shown in FIG. 1. FIG. 1 clearly shows that a heat crack tendency decreases with increasing yttrium content. However, with increasing yttrium content in a magnesium alloy the risk also increases that an implant of the magnesium alloy dissolves in the body after a predetermined time, but yttrium remains. For this reason with a use of corresponding magnesium alloys for implants an yttrium content is limited to a maximum of 0.6%, preferably less than 0.5%.

Corresponding results were obtained for magnesium alloys in which yttrium was replaced by ytterbium, likewise for magnesium alloys with gadolinium. In other words: it was possible to clearly reduce a heat crack tendency in all cases, wherein the ytterbium or gadolinium contents could be twice as high as the yttrium contents. This can be attributed to the fact that intermetallic phases form with the three referenced elements, wherein due to the atomic masses the contents of ytterbium and/or gadolinium can be much higher than those of yttrium.

Through an alloying of yttrium, ytterbium and/or gadolinium the solidus line of a magnesium zinc alloy can be raised, which leads to a reduction of the heat crack tendency of a magnesium alloy of this type. This is illustrated in FIG. 2. As can be seen, a number of heat cracks is reduced with decreasing melt interval, wherein favorable results are already achieved with yttrium contents of less than 0.5%.

FIG. 3 shows a calculated isothermal section at 300° C. for magnesium zinc alloys with 3.0% zinc, 0.3% zirconium and different contents of yttrium and gadolinium. The temperature of 300° C. corresponds to a typical extrusion temperature. As can be seen, with yttrium contents up to 0.6% only a low-yttrium intermetallic phase $Mg_3YZn_6$ is present, while with higher yttrium contents an yttrium-rich phase $MgYZn_3$ is also present. The low-yttrium phase is considered to be more favorable for biodegradable implants, if an intermetallic phase should not dissolve or dissolve only very slowly in the body, since a local concentration is then lower. Furthermore, a better solubility of the low-yttrium phase is also assumed.

The isothermal section according to FIG. 3 also shows that gadolinium can also be present in addition to yttrium without anything changing in the nature of the yttrium phases. In particular high gadolinium contents can be provided even without negative interaction, wherein the solubility of the intermetallic phases does not change.

Magnesium alloys according to the invention, as mentioned, were also produced by continuous casting, wherein an average grain size of the structure as well as in the permanent-mold casting for all of the magnesium alloys according to the invention was less than 50 μm. Through a subsequent annealing at an annealing temperature of 280° C. to 400° C. and a subsequent extrusion molding of parts of the extrusion-molded magnesium alloys, a further reduction of the grain size could be achieved. In particular magnesium alloys with ytterbium, for example, a magnesium zinc alloy with 2% ytterbium, showed high strengths as well as high elongation at break (yield strength $R_{p0.2}$ approx. 300 MPa, elongation at break $A_f$ approx. 25%). Magnesium alloys with such favorable property values are suitable not only for the production of biodegradable implants, but can also be used in particular for a production of thermally and/or mechanically highly stressed components, for example components of motor vehicles which in use are subjected to a high static and/or dynamic load.

The invention claimed is:

1. A magnesium alloy, containing (in % by weight):
   more than 0.0% zinc to 7.0% zinc,
   0.0 to 1.0% zirconium,
   0.0 to 1.0% calcium,
   0.0 to 1.0 manganese,
   0.0 to 0.5% silicon,
   0.0 to 1.0% silver,
   up to 0.5% aluminum,
   more than 0.1 to 0.8% yttrium,
   and at least one element selected from the group comprising
   0.05 to 4.0% ytterbium and
   0.05 to 4.0% gadolinium;
   the residue being magnesium and impurities due to production.

2. The magnesium alloy according to claim 1, containing 1.0 to 5.0% zinc.

3. The magnesium alloy according to claim 1, containing 0.1 to 0.6% zirconium and/or 0.1 to 0.4% calcium.

4. The magnesium alloy according to claim 3, wherein a sum content of zirconium and calcium is 0.6 to 1.0%.

5. The magnesium alloy according to claim 1, containing at least one element selected from the group comprising:
   0.1 to 0.5% manganese,
   0.1 to 0.5% silicon, and
   0.1 to 0.5% silver.

6. The magnesium alloy according to claim 1, containing at least one element selected from the group comprising:
   more than 0.1 to less than 0.5% yttrium,
   0.1 to 1.2% ytterbium, and
   0.1 to 1.2% gadolinium.

7. The magnesium alloy according to claim 1, containing at least two elements selected from the group yttrium, ytterbium and gadolinium, wherein a sum content of these elements is less than 2.5%.

8. A biodegradable implant comprising a magnesium alloy according to claim 1.

9. An implant of a magnesium alloy according to claim 1.

10. The magnesium alloy according to claim 1, containing 2.5 to 4.5% zinc.

11. The magnesium alloy according to claim 1, containing 0.4 to 0.8% yttrium.

12. The magnesium alloy according to claim 1, containing at least 1.0% zinc.

13. The magnesium alloy according to claim 1, containing at least 0.1% calcium.

14. A method for producing a body, in particular an implant, from a magnesium alloy, comprising:
   a) producing a melt containing:
   more than 0.0% zinc to 7.0% zinc,
   0.0 to 1.0% zirconium,
   0.0 to 1.0% calcium,
   0.0 to 1.0% manganese,
   0.0 to 0.5% silicon,
   0.0 to 1.0% silver,
   up to 0.5% aluminum,
   more than 0.1 to 0.8% yttrium,
   and at least one element selected from the group comprising
   0.05 to 4.0% ytterbium and
   0.05 to 4.0% gadolinium
   the residue being magnesium and impurities due to production;

b) casting the melt to form a solid mass;
c) annealing the solid mass;
d) optionally shaping the solid mass or a part thereof; and
e) producing the body from the shaped or unshaped mass or parts thereof.

15. The method according to claim 14, wherein the annealing is carried out at an annealing temperature of 280° C. to 400° C.

16. The method according to claim 14, wherein a shaping is carried out at a temperature below the annealing temperature.

17. The method according to claim 14, wherein the shaping is carried out by extrusion molding, equal channel angular pressing and/or forging.

18. The method according to claim 14, wherein the melt contains 0.4 to 0.8% yttrium.

19. The method according to claim 14, wherein the melt contains at least 1.0% zinc.

20. The method according to claim 14, wherein the melt contains at least 0.1% calcium.

* * * * *